US011090159B2

(12) United States Patent
Nathe et al.

(10) Patent No.: US 11,090,159 B2
(45) Date of Patent: Aug. 17, 2021

(54) HEART IMPLANT

(71) Applicant: coramaze technologies GmbH, Hilden (DE)

(72) Inventors: Niklas Maximilian Nathe, Düsseldorf (DE); Stefan Daniel Menzl, Hersbruck (DE); Thomas Gerhardt, Munich (DE); Raz Bar-On, Hadera (IL); Leah Kidney, Munich (DE)

(73) Assignee: coramaze technologies GmbH, Hilden (DE)

( * ) Notice: Subject to any disclaimer, the term of this patent is extended or adjusted under 35 U.S.C. 154(b) by 103 days.

(21) Appl. No.: 16/394,014

(22) Filed: Apr. 25, 2019

(65) Prior Publication Data
US 2019/0247190 A1  Aug. 15, 2019

Related U.S. Application Data

(63) Continuation of application No. PCT/EP2016/001794, filed on Oct. 28, 2016.

(51) Int. Cl.
*A61F 2/24* (2006.01)

(52) U.S. Cl.
CPC ............ *A61F 2/246* (2013.01); *A61F 2/2442* (2013.01); *A61F 2/2466* (2013.01);
(Continued)

(58) Field of Classification Search
CPC ...... A61F 2/2418; A61F 2/2487; A61F 2/246; A61F 2/2466; A61F 2/2439
See application file for complete search history.

(56) References Cited

U.S. PATENT DOCUMENTS

| 2004/0127982 A1* | 7/2004 | Machold | A61F 2/2454 623/2.36 |
| 2006/0058871 A1* | 3/2006 | Zakay | A61F 2/246 623/2.18 |

(Continued)

FOREIGN PATENT DOCUMENTS

| CN | 101056596 | 10/2007 |
| CN | 103189015 | 7/2013 |
| WO | WO 2018/077371 | 5/2018 |

OTHER PUBLICATIONS

International Preliminary Report on Patentability dated May 9, 2019 From the International Bureau of WIPO Re. Application No. PCT/EP2016/001794. (9 Pages).

(Continued)

*Primary Examiner* — Suba Ganesan

(57) ABSTRACT

The invention relates to a heart implant comprising an attachment element (2), particularly a tubular attachment element for attaching a sheath (4), preferably having a sheath (4) being coaxially positioned around at least a part of the attachment element (2) and fixed to it, the attachment element (2) having a lower end (2a) and an upper end (2b) and several strips (3) at least at one of the ends, preferably being split into several strips at least at one of the ends (2b), preferably only at the upper end (2b), the strips (3) forming an expandable anchoring cage, particularly for fixing the heart implant to a lumen of the heart, preferably the atrium, by surface contact between an exterior surface of the expandable cage and an interior lumen surface, the strips (3) of the anchoring cage ending in respective strip tips (7) at the end of their extension in the compressed state, particularly during delivery through a catheter (1), the strip tips (7) forming the distal or proximal end of the implant, particularly a distal end being released first out of the catheter, wherein the implant furthermore comprises a fixation means (Continued)

(5, 6) to which each respective strip tip (7) is releasable fixed, preferably furthermore comprising a releasing means (9) for releasing the connection between fixation means (5, 6) and strip tips (7).

4 Claims, 4 Drawing Sheets

(52) U.S. Cl.
CPC .......... *A61F 2/2487* (2013.01); *A61F 2/2439* (2013.01); *A61F 2220/0025* (2013.01); *A61F 2220/0075* (2013.01); *A61F 2230/0071* (2013.01); *A61F 2230/0093* (2013.01); *A61F 2250/0003* (2013.01)

(56) References Cited

U.S. PATENT DOCUMENTS

| | | | | |
|---|---|---|---|---|
| 2011/0066233 | A1* | 3/2011 | Thornton | A61B 17/00234 623/2.11 |
| 2012/0197389 | A1 | 8/2012 | Alferness et al. | |
| 2014/0249621 | A1 | 9/2014 | Eidenschink | |
| 2015/0039084 | A1 | 2/2015 | Levi et al. | |
| 2016/0242902 | A1 | 8/2016 | Morriss et al. | |
| 2017/0065418 | A1* | 3/2017 | Skarsgard | A61F 2/2487 |
| 2017/0266003 | A1* | 9/2017 | Hammer | A61F 2/2418 |

OTHER PUBLICATIONS

International Search Report and the Written Opinion dated Jul. 6, 2017 From the International Searching Authority Re. Application No. PCT/EP2016/001794. (13 Pages).

Notification of Office Action and Search Report dated Aug. 28, 2020 From the National Intellectual Property Office of the People's Republic of China Re. Application No. 201680091814.8 and Its Machine Translation of Office Action Into English. (13 Pages).

\* cited by examiner

HEART IMPLANT

RELATED APPLICATION(S)

This application is a Continuation of PCT Patent Application No. PCT/EP2016/001794 having International filing date of Oct. 28, 2016, the contents of which are incorporated by reference as if fully set forth herein in their entirety.

FIELD AND BACKGROUND OF THE INVENTION

The invention relates to a heart implant, particularly a heart implant being configured to reduce or eliminate a heart valve insufficiency after implantation into the heart.

Typically, such implants are positioned in such a way that a closure element of the implant is situated in the valve annulus and closes a remaining gap of the closed valve leaflets. For that purpose, the closure element is connected to at least one anchoring cage being configured to fix the closure element within the heart in the desired position i.e. in the valve annulus preferably to be contacted by the closing valve leaflets.

In a possible embodiment known from applicants own prior patent filings the closure element may be formed by an inflatable sheath I membrane that is positioned, preferably coaxially positioned around an attachment element, preferably a tubular attachment element and fixed to this attachment element at the respective ends of the sheath I membrane to get a fluid tight space around the attachment element. Such a fluid tight sheath may be inflated with a fluid.

In another embodiment known from applicants own prior patent filings the closure element may be also formed of a sheath/membrane being supported by an expanded part of an attachment element, preferably tubular attachment element.

By expanding the attachment element also the sheath expands in cross section and contacts the underlying scaffold structure formed by the expanded attachment element. The sheath also here prevents blood from passing through the valve in a closed leaflet state and may be also fluid tight. But in this case the sheath is not necessarily fluid tight from the beginning of implantation. The sheath may have pores for allowing blood to enter but may not allow clotted blood to escape from the inner space of the sheath or expanded attachment element. The blood may get clotted more and more by time and may close the sheath and thus formed closure element accordingly.

The implant of the invention comprises a closure element of any kind and preferably comprises a closure element as mentioned before.

It is known in the state of the art to use an anchoring element punctured into the myocardium of the ventricle for fixation of the closure element. Besides this invasive way modern implants provide a less invasive fixation just by contacting the interior wall of the atrium with the outer surface areas of an anchoring element formed of an expanded cage that is connected to the closure element. Such cage typically is in a collapsed state for feeding the entire implant through a catheter into the heart where it is expanded after release from the catheter for fixation purposes. The invention relates to such implants having an expandable, preferably mesh-like cage formed of strips for anchoring purposes.

A cage may also be formed without meshes, particularly just by several side-by-side-lying strips having no interconnection. The invention in general also relates to non-meshed cages.

The strips of the cage may be attached to the closure element in any known way. Cage and attachment element as mentioned before may be separate element that have been connected but may also be integrally formed of the same origin element. For example, the strips may be formed by splitting such element.

It is furthermore known from applicants own prior patent filings that the attachment element, preferably tubular attachment element has a lower end and an upper end and is split into several strips at least at the upper end, the strips forming an expandable cage, particularly for fixing the heart implant to the atrium of the heart by surface contact between an exterior surface of the expandable cage (the several strips) and an interior atrium surface.

No matter how the cage is connected to the closure element or its attachment element, the strips may be formed of strands, braided wires, synthetic braids or reinforced resorbable scaffolds.

The mentioned positions "lower" and "upper" or directions mentioned in this disclosure are to be understood in the intended position of the implant if it is correctly implanted in the heart. In the heart the atrium is positioned above the ventricle and accordingly the lower end of the attachment element faces the ventricle, particularly is positioned in the ventricle and the upper end faces the atrium, particularly is positioned in the atrium if correctly implanted.

The attachment element, particularly the tubular attachment element and the strips of an anchoring cage may originate from one single tube by cutting the tubular wall several times, preferably in an axial direction the mentioned strips all start their extension from an annular upper end area of the attachment element and preferably are equally spaced along the circumference of this end. Such a cage may also be formed of strips starting their extension at the lower end of the attachment element.

An anchoring cage is preferably formed by splitting and merging strips thus forming a half mesh between the points of splitting and merging. This embodiment is also preferred for the invention described in this disclosure.

A cage having several meshes is formed that way for solely fixing the heart implant to the atrium and/or ventricle of the heart by surface contact between the exterior cage surface and the interior surface of the respective heart lumen (atrium or ventricle). Preferably the invention relates to an implant having a cage only on the atrial side of the closure element.

A cage being formed of several expanded strips, preferably originating from a cut tube, by radial expansion provides the advantage that the strips may generate a radial force being essentially perpendicular to the axis of extension of the (tubular) attachment element to keep the anchoring cage in place after implantation and expansion. The anchoring cage is sufficiently compliant in radial direction in order to adapt its shape to the atrium.

Such anchoring cages may have strip tips, preferably free strip tips, at the end of the extension of strips that may cause puncture of the myocard during the implantation process since these tips may be released out of a delivery catheter without direct control by the surgeon from the outside of the patient. A strip tip is understood to be free if it is not permanently connected to another structure, particularly another strip tip. Accordingly, a part of the strip near the strip tip may generally move independent of other parts of the anchoring cage.

The implant of the invention may generally have any kind of cage comprising strip tips and preferably a cage construction as mentioned before.

It is therefore an object of the invention to provide a heart implant for mammalian patients, preferably humans, having improved controllability in regard to the position of the strip tips during the process of implantation. Preferably it is an object to provide temporarily a connection of the strip tips to another structure that serve to control the release of the strip tips out of a catheter.

Even though the application of the implant and method is preferred in regard to humans the implant and method of treatment may be also applied to animals, particularly mammalian animals.

SUMMARY OF THE INVENTION

The object is solved by a heart implant comprising an attachment element, particularly a tubular attachment element for attaching a sheath, preferably having a sheath being coaxially positioned around at least a part of the attachment element and fixed to it, the attachment element having a lower end and an upper end and several strips at least at one of the ends, preferably being split into several strips at least at one of the ends, preferably only at the upper end, the strips forming an expandable anchoring cage, particularly for fixing the heart implant to a lumen of the heart, preferably the atrium, by surface contact between an exterior surface of the expandable cage and an interior lumen surface, the strips of the anchoring cage ending in respective strip tips at the end of their extension, and in the compressed state, particularly during delivery through a catheter, the strip tips forming the distal or proximal end of the implant, particularly forming the distal end being released first out of the catheter, wherein the implant furthermore comprises a fixation means to which each respective strip tip is releasable fixed. Preferably the implant furthermore comprises a releasing means for releasing the connection between fixation means and strip tips.

Accordingly release of the connection between a respective strip tip and a fixation means may be performed by a separate releasing element or automatically, for example if a threshold force or torque is applied to the fixation means'.

It is an essential feature of the invention to prevent the strip tips of the at least one anchoring cage from arbitrary expanding, particularly if the strips of the cage or also the attachment element are made of nitinol, known for its superelastic capabilities.

Preferably the fixation means is configured to constrain all strip tips from uncontrolled expansion, particularly at least during the first stage of release of the implant out of a catheter if the strip tips are released first or at least during the last state of release of the implant out of the catheter if the strip tip are release last. As an example this may be performed by bundling I holding together all strip tips.

Preferably bundling I holding together may be understood as a situation in which the strips tips are all contacting each other.

It may be provided this way, that all the strip tips emerging from the catheter tip simultaneously are commonly drawn into a specific direction using the fixation means, particularly if the tips are released first. For example, a surgeon may fix the fixation means in position relative to the catheter or may pull on the fixation means thus exerting a pulling force to the strip tips during release out of the catheter.

According to an improvement the fixation means, preferably also the releasing means extend through the catheter along the entire catheter length between the implant and the proximal end of the catheter and are operable at the proximal end of the catheter, particularly by a surgeon.

According to a preferred embodiment the fixation means and/or the releasing means are operable at least by pulling or turning. Pulling the fixation means will preferably keep the strip tip in a bundled configuration. Releasing the pulling force may allow the strip tips to separate from each other according to their teached-in shape, if a shape memory material is chosen for the strips, like the mentioned nitinol. So gently releasing the pulling force may result in an improved control over the strip tip separation, what may be visually controlled in live x-ray images.

Operating, particularly pulling the releasing means will disconnect the fixation means and the strip tip from each other and the anchoring cage is free to attain its shape.

Preferably a respective strip tip comprises a connecting means for connecting the fixation means to it. The connecting means may be formed of an orifice or a gripping element at the strip tip. An orifice may be formed by a through hole I pinhole passing through the strip material or a bent part of the strip tip forming a loop, preferably bent over at least 270 degrees. A gripping element may be formed of a thickening. A connecting means may also be formed of a bulbous element being constrainable by a fixation means, particularly a slotted structure of a fixation means.

In a first embodiment the fixation means may comprise several fixation elements, each element having a claw at its end and each claw being connectable to a gripping element and openable by operating the releasing means.

In another embodiment a fixation element may also comprise a slotted structure for constraining a bulbous element at the strip tip.

In another preferred embodiment the fixation means comprises several fixation elements, each fixation element being fed through a respective orifice of a strip tip from one side of the orifice to the other side of the orifice and being prevented from being pulled out of the orifice by a force or torque that needs to be overcome or by the releasing means, particularly the releasing means passing through the fixation means at the other side. Preferably when pulling the fixation means the releasing means is urged towards the strip tip and held in place by friction unless the releasing means is operated, particularly pulled. In this configuration the releasing means is preferably oriented perpendicular to the normal vector of the orifice plane.

A fixation element is preferably formed of a fixation strip, particularly made of metal, having an orifice at the fixation strip end, particularly the orifice being adapted to have a releasing means passing through the orifice. The cross section of such fixation strip is configured so that it can pass through the orifice of the respective strip tip.

In another embodiment the fixation element may be provided by a suture guided to form a 180-degree loop, the loop and the two essentially parallel suture part being fed through the orifice of the strip tip. The loop now form another orifice for feeding through the releasing means.

In general, the releasing means may be provided by single suture that is used to release all strip tip and fixation means, particularly all fixation elements. When pulling the release suture the connection between the strip tip and fixation means is disengage one after the other. The releasing means may be pulled entirely out of the catheter.

In order to restrict the pulling distance for totally disengaging all connection it may be provided that the releasing means is a suture having two ends. The first end being positioned outside the patient in front of the proximal end of the catheter and the second end being positioned in the catheter near the distal end of the catheter. An intermediate part of the suture near the second end is fed through the respective orifices of fixation means all of the fixation elements.

In another embodiment the releasing means may have several releasing elements, each releasing element being associated to a respective fixation means for releasing it upon operation, i.e. pulling the releasing means. In such a case each releasing element may be formed of a suture guide passing through an orifice of the respective fixation element. All of the several releasing element may be connected to a single common releasing handle. In his case it is only the releasing handle that is fed through the catheter the entire catheter length. The releasing handle may be formed of a single suture or pulling wire.

In a preferred embodiment the fixation means comprises a handling element being common to all fixation elements, particularly all fixation elements being attached to the handling element. All fixation elements may be attached to the distal end of the handling element along the circumferential periphery in an equally spaced fashion.

The handling element may be formed of a sleeve I hose running through the entire catheter and being operably at the proximal end of the catheter, particularly the hose I sleeve surrounding the implant at least partially, preferably surrounding the entire implant prior to release into the heart lumen. For example, for releasing the implant out of the catheter the hose shaped handling element may be fixed in position and the implant pushed forward thus also moving the implant relative to the handling element and furthermore thus exerting a force pulling backwards if the fixations elements get stretched. By performing this operation the strip tips get bundled. Now the implant and the handling element may be pushed forwards to move the implant but to keep the tips bundled. Only pushing the handling element will release the pulling force and the strip tip may separate and expand.

The strip tips may comprise a bent part, the convex part of it facing the inner catheter wall in the compressed state and if the implant is positioned in the catheter. This may serve to reduce friction between the implant and the catheter.

Accordingly, the bent part may be gliding on the inner catheter wall during transportation of the implant in the catheter.

The invention may be used in connection with generally any kind of anchoring cage construction having the aforementioned problems.

In a possible embodiment in an expanded state the strips of the anchoring cage may extend away from the upper and lower end of the attachment element and increase their radial distance to the central axis of the attachment element in a first part of extension and decrease their distance to the central axis of the attachment element in a second part of extension and ending in the strip tips above the upper part of the attachment element. Such a cage is entirely positioned above the upper end of the attachment element. The strip tips may be also positioned in the top area of the entire implant and may harm the upper myocard in the atrium or pulmonary vessels situated there if they are not controlled in expansion.

In another preferred embodiment in an expanded state the strips extend from the upper end, particularly after a bent of 180 degrees, towards the lower end of the tubular attachment element and form an expanded cage being positioned around at least an upper part of the tubular attachment element.

In both embodiments the strips, preferably each strip along its extension from the upper end of the attachment element towards the strip tip comprises split strip regions in which the strip branches into two strips and merged strip regions, in which two strips, in particular respectively formed of at least one of the strips split beforehand, are merged into one strip. Meshed are formed this way providing an interconnected cage construction.

The invention may serve to treat heart valve insufficiency of a diseased heart valve having a remaining gap between closed valve leaflets by delivering a heart implant as explained via a catheter to the heart of a mammalian patient, preferably a human, releasing an anchoring cage of the implant at least partly out of the catheter into the heart, constraining the strip tips of the cage forming strips from uncontrolled expansion, particularly by bundling together by using the fixation means, particularly by pulling the fixation means, further releasing the anchoring cage out of the catheter and positioning the implant such that the anchoring cage is arranged in the atrium of the heart and the attachment element having a sheath/membrane attached to it passes through the valve annulus, anchoring the implant to the atrium by expanding, particularly self-expanding the anchoring cage and thus forcing the exterior surface of the cage to contact the inner heart wall of the atrium, disengaging the fixation means from the strip tips by operating, particularly pulling the releasing means, reducing blood regurgitation by expanding the sheath/membrane and thus preventing or reducing the remaining gap between the closed valve leaflets, removing the fixation means, releasing means and afterwards the catheter.

The implant of the invention may be used no matter whether the implantation process is retrograde or antegrade. Particularly it is possible to release the cage forming strips first out of the catheter with the remaining part of the implant following or vice versa. Accordingly the implant may be transported through the catheter having the strip tips facing the implantation site or having the closure element facing the implantation site.

BRIEF DESCRIPTION OF THE SEVERAL VIEWS OF THE DRAWINGS

Preferred embodiments of the invention are described in connection with the attached figures.

DESCRIPTION OF SPECIFIC EMBODIMENTS OF THE INVENTION

Figure 1:
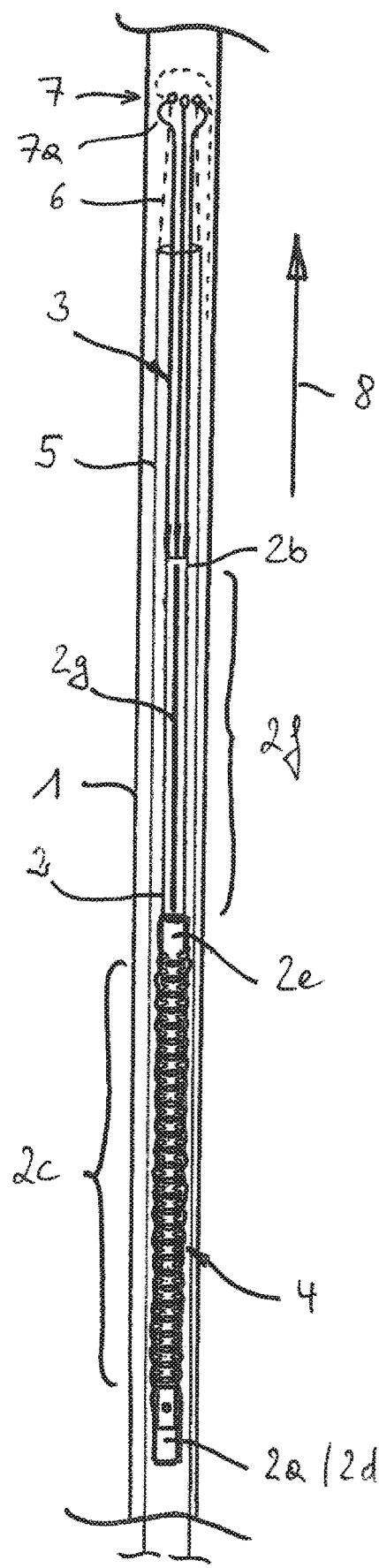
FIG. 1: showing a preferred embodiment in a first state of implantation.

FIG. 1 shows an implantation situation in which an implant is positioned in a catheter 1. The implant comprises a tubular attachment element 2 having a lower end 2a and an upper end 2b. At the upper end the attachment element is split into several strips 3, only three of them are depicted just for better visibility. More than three may be provided here. These strips 3 will form an anchoring cage after expansion.

FIG. 1 shows the crimped or compressed state of the implant. A lower part 2c of the attachment element 2 is surrounded by sheath 4 that may have the shape of a hose. The two ends of the sheath are tightly attached to the attachment element 2 in the spaced tubular areas 2d and 2e.

After inflating the sheath 4, particularly through a valve in lower end 2a of the attachment element 1 the inflated sheath 4 forms a closure element that may be positioned in the valve annulus of the heart, preferably the mitral valve.

The upper part 2f of the attachment element 2 will be later surrounded by the expanded cage.

During implantation the implant and a hose shaped handling element 5 are guided in the catheter 1 and may be pushed in direction 8. At the distal end of this handling element 5 several fixation sutures 6 are attached to the handling element 5. The fixation sutures are depicted as dashed lines. The other end of each fixation suture is releasable connected to the strip tip 7 of a strip that forms the cage.

Figure 2:
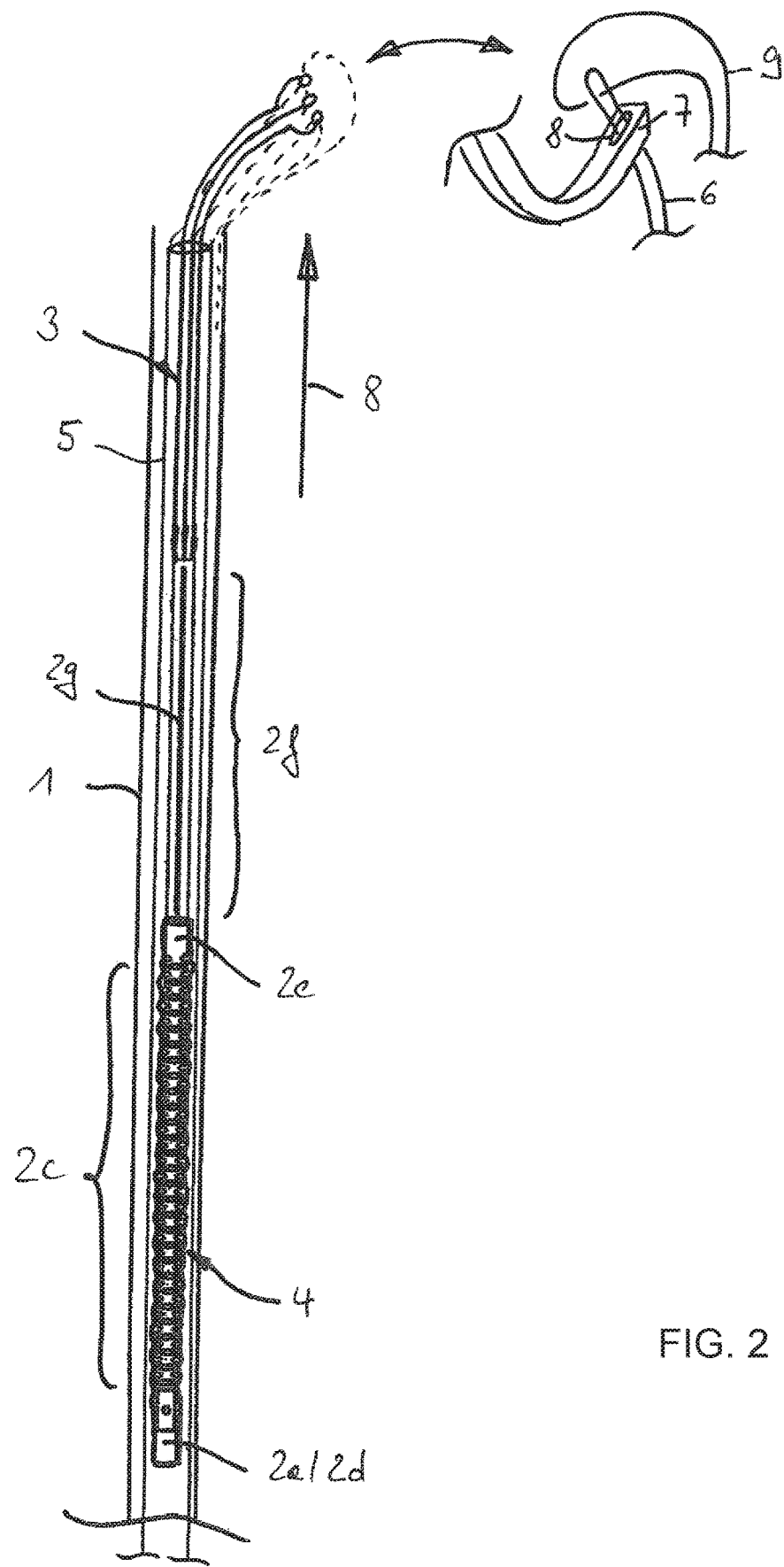
FIG. 2: showing the same embodiment in a second state.

As shown in the enlarged view of FIG. 2 the strip tip 7 comprises a pinhole 8 and a 180-degree loop of each fixation suture 6 is fed from one side of the pinhole through this pinhole 8 to the other side. On the other side a releasing suture 9 is fed through the loop of the fixation suture 6 thus preventing that the fixation suture may be pulled back. One single and common release suture 9 may be used for all fixation sutures 6. At least one end of the releasing suture 9 runs through the entire catheter length and may be pulled by a surgeon at the proximal side of the catheter 1. The other end may remain in the catheter near the distal end of it.

FIG. 1 shows that a respective strip tip 7 comprises a bent part 7a, the convex part of it may glide on the inner surface of the catheter 1 and thus reduces friction due to the small contact area.

The upper part of the attachment element comprises at least one slit 2g in axial direction for better bendability of this part. The lower part also comprises slits in different orientation for bendability.

FIG. 2 depicts a situation of partial release of the implant out of the catheter 1. The strip tips 7 are release but bundled together by pulling the handling element 5. Accordingly, a pulling force is exerted to all strip tips 7 and they bent all into the same direction thus being prevented from separation and uncontrolled expansion. The implant may be further released and positioned in the heart with keeping the strip tips 7 bundled together.

Figure 3:
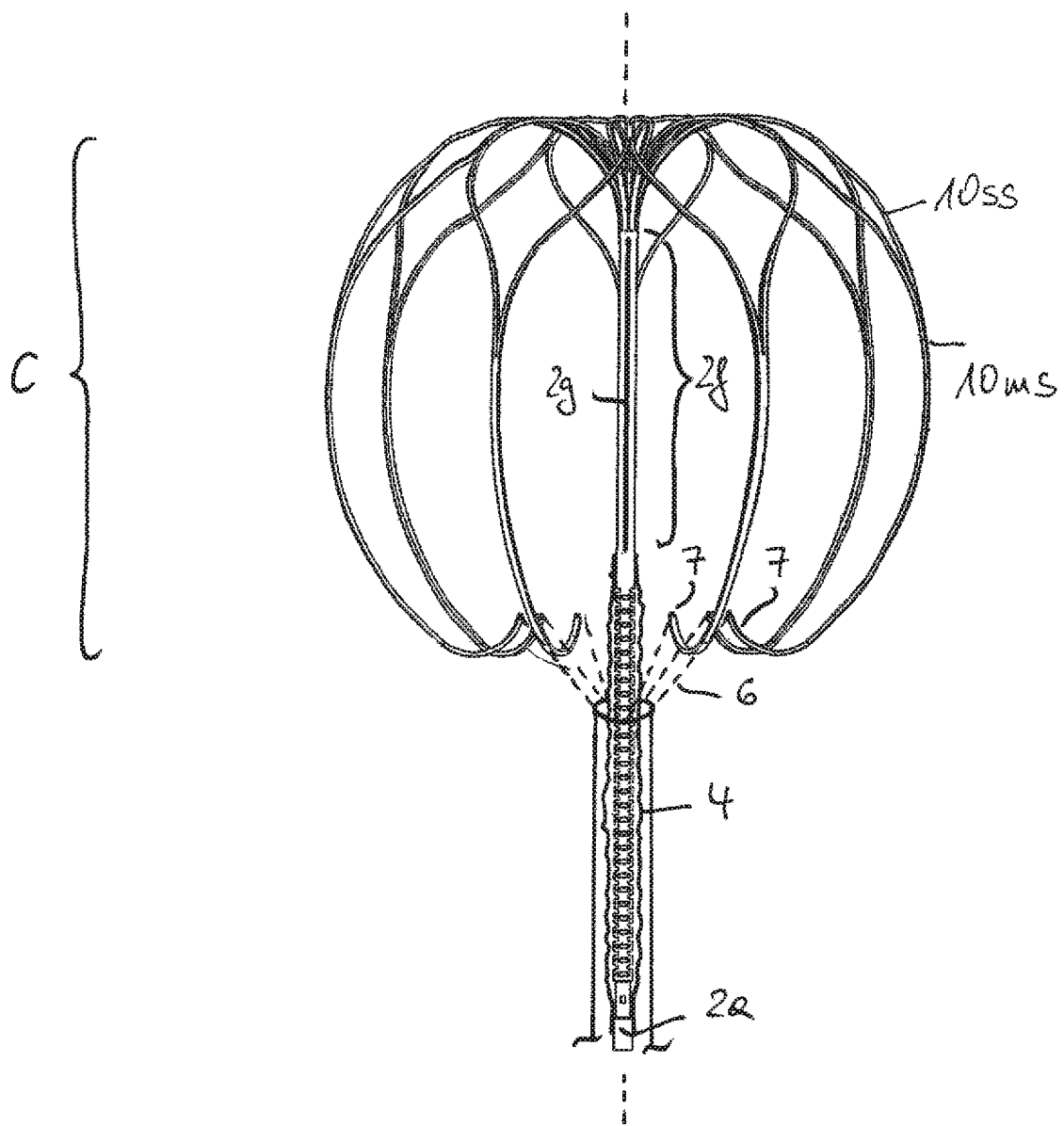
FIG. 3: showing the same embodiment in a third state.

FIG. 3 now shows the situation in which the cage is fully released from the catheter (not shown here) and already expanded. As can be seen the cage C is partially surrounding the tubular attachment element 2 and the closure element formed of the inflatable sheath 4 that I not yet inflated in this depiction. The strips 10 of the cage C are extending from the top end of the tubular attachment element via a 180 degree bent towards the lower end 2a.

The strips 9 comprise split strip regions 1Oss and merges strip region 1Oms.

The release suture 9 is not shown for better visibility but may now be pulled out of all loops of the fixation sutures 6 in order to disengage them from the strip tips 7. Afterwards the handling element 5 may be pulled out of the catheter and the closure element may be expanded by inflating the sheath 4.

In contrast to FIGS. 1 and 2 the strip tip 7 do not have a bent part 7a, but they may have.

Figure 4:
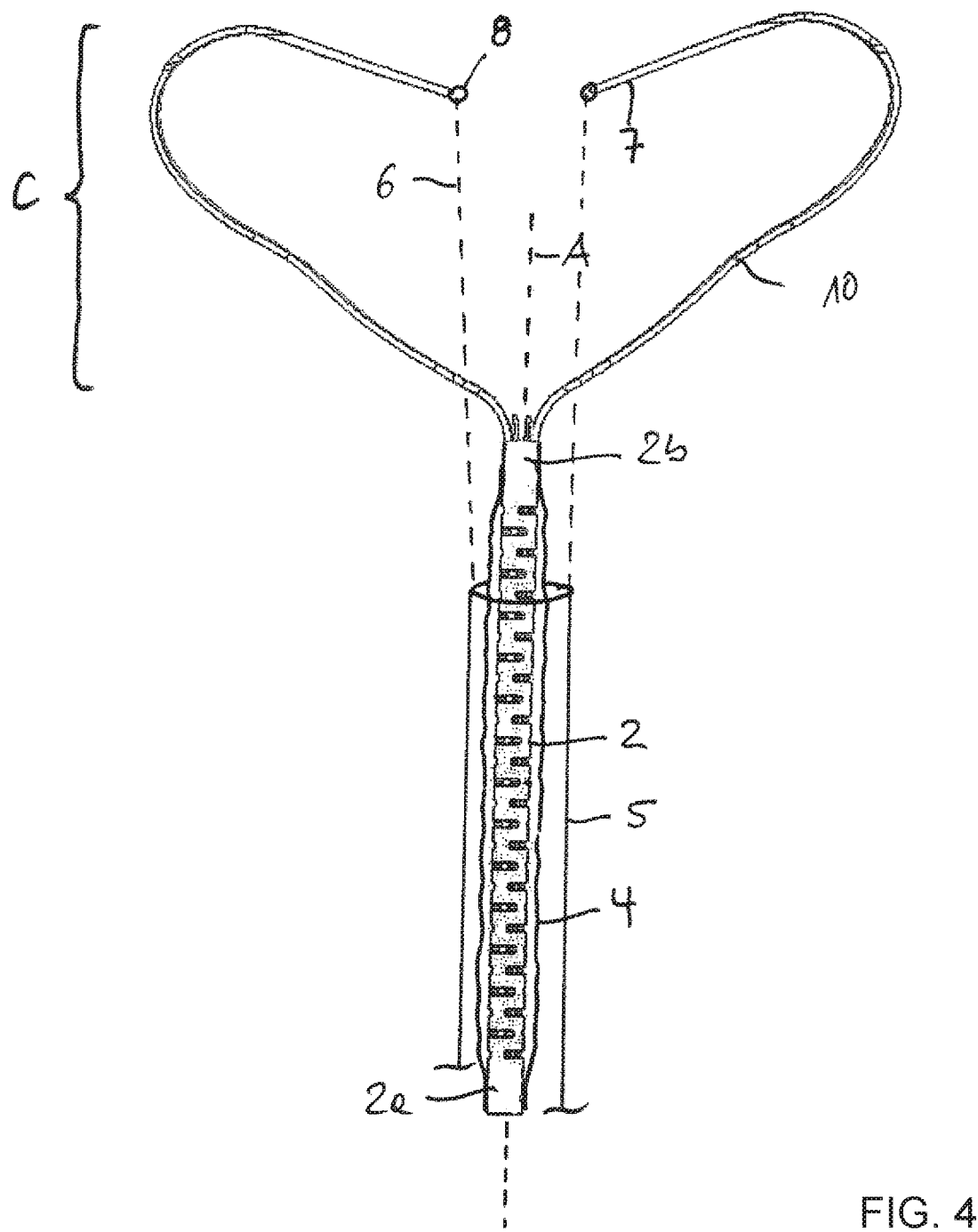
FIG. 4: showing a second embodiment of a different anchoring cage

FIG. 4 just shows a different kind of anchoring cage C. This cage C comprises several strips 10, just two of them are shown for better visibility in this view. The strips 10 are all extending away from the upper and lower end 2a, 2b of the attachment element 2, in a first lower part increasing in radial distance to the axis A of the attachment element 2 and in a second part decreasing a radial distance again. All strip tips 7 having pinholes 8 are above the attachment element 2 or closure element formed by the inflatable sheath 4. The strips 10 may have merged and split strip regions.

Also here it is shown that in the end stage of releasing the implant out of the catheter (not shown here) the cage is already fully released and expanded after controlling the release and expansion as described in FIGS. 1 and 2, that in principle is also applicable here.

The not shown common release suture may now be pulled and the connection of the strip tips 7 and fixation sutures 6 disengaged. Each fixation suture 6 is depicted as a dashed line but may be realized by a closed loop of a single suture, being connected at the lower end to the handling element 5 and at the upper end to the pinhole 8.

What is claimed is:

1. A heart implant comprising a closure element including an inflatable sheath and having a lower end and an upper end, said closure element being attached to an expandable anchoring cage formed from several strips with each strip being split into two strip branches that subsequently merge into a single strip as each strip extends in a direction of an upper region of the implant, the expandable anchoring cage being for fixing the heart implant to a lumen of an atrium via surface contact between an exterior surface of the expandable cage and an interior surface of the atrium, such that said closure element is positioned within an annulus of a valve having leaflets to allow said leaflets to move between an open position and a closed position and prevent or reduce a remaining gap between said closed position of said leaflets of said valve when inflated;

wherein the implant further comprises a fixation element releasably attached to a tip of each strip, and a releasing mechanism for releasing the fixation element from the tips.

2. The heart implant according to claim 1, wherein the fixation element is configured to radially constrain the strips.

3. The heart implant according to claim 1, wherein each tip comprises a connector for connecting to the fixation element.

4. The heart implant according to claim 3, wherein the fixation element includes a suture.

* * * * *